(12) United States Patent
Fitzpatrick

(10) Patent No.: US 11,844,699 B2
(45) Date of Patent: Dec. 19, 2023

(54) METHOD OF MAKING A PROSTHETIC INTERVERTEBRAL DISC JOINT ASSEMBLY

(71) Applicant: Fitzbionics Limited, Surrey (GB)

(72) Inventor: Noel Fitzpatrick, Surrey (GB)

(73) Assignee: Fitzbionics Limited, Surrey (GB)

( * ) Notice: Subject to any disclaimer, the term of this patent is extended or adjusted under 35 U.S.C. 154(b) by 0 days.

(21) Appl. No.: 18/347,272

(22) Filed: Jul. 5, 2023

(65) Prior Publication Data
US 2023/0338158 A1 Oct. 26, 2023

Related U.S. Application Data

(63) Continuation of application No. 17/353,915, filed on Jun. 22, 2021, now abandoned, which is a continuation of application No. 15/513,689, filed as application No. PCT/GB2015/052776 on Sep. 24, 2015, now abandoned.

(30) Foreign Application Priority Data

Sep. 24, 2014 (GB) .................................. 1416867

(51) Int. Cl.
*A61F 2/44* (2006.01)
*A61F 2/30* (2006.01)

(52) U.S. Cl.
CPC ........ *A61F 2/4425* (2013.01); *A61F 2/30771* (2013.01); *A61F 2002/305* (2013.01); *A61F 2002/307* (2013.01); *A61F 2002/30084* (2013.01); *A61F 2002/3093* (2013.01); *A61F 2002/30387* (2013.01); *A61F 2002/30528* (2013.01); *A61F 2002/30654* (2013.01); *A61F 2002/30777* (2013.01); *A61F 2002/30787* (2013.01); *A61F 2002/30884* (2013.01);
(Continued)

(58) Field of Classification Search
CPC ................................................ A61F 2/44–447
See application file for complete search history.

(56) References Cited

U.S. PATENT DOCUMENTS 5,425,773 A   6/1995 Boyd
5,674,296 A  10/1997 Bryan
(Continued)

FOREIGN PATENT DOCUMENTS

EP     2609896       3/2013
WO  2006/063354    6/2006

OTHER PUBLICATIONS

EP15774660, Notice of Allowance dated Jun. 6, 2023, 46 pages.

*Primary Examiner* — Eduardo C Robert
*Assistant Examiner* — Steven J Cotroneo
(74) *Attorney, Agent, or Firm* — Andrus Intellectual Property Law, LLP

(57) ABSTRACT

A prosthetic intervertebral disc joint assembly for replacing at least a portion of an intervertebral disc between first and second adjacent vertebrae. A first component has an intervertebral portion insertable between adjacent vertebrae, with a bone-engaging side and a convex articulating inner side opposite the bone-engaging side. A second component engages the second vertebra and has a concave articulating surface. The first and second components each include a fixation portion for securing the component to the anterior side of the respective vertebra.

15 Claims, 9 Drawing Sheets

(52) U.S. Cl.
CPC . *A61F 2002/443* (2013.01); *A61F 2002/4435* (2013.01); *A61F 2310/00023* (2013.01)

(56) References Cited

U.S. PATENT DOCUMENTS

| | | | |
|---|---|---|---|
| 6,113,637 A * | 9/2000 | Gill | A61F 2/4611 |
| | | | 623/17.15 |
| 7,494,507 B2 | 2/2009 | Dixon | |
| 7,867,276 B2 | 1/2011 | Matge et al. | |
| 7,905,922 B2 | 3/2011 | Bergeron | |
| 7,927,374 B2 | 4/2011 | Duggal | |
| 8,038,716 B2 * | 10/2011 | Duggal | A61F 2/4657 |
| | | | 623/17.14 |
| 8,070,777 B2 | 12/2011 | Soboleski | |
| 8,172,877 B2 * | 5/2012 | Winslow | A61F 2/4684 |
| | | | 606/247 |
| 8,282,681 B2 | 10/2012 | McLeod et al. | |
| 8,979,932 B2 | 3/2015 | Rashbaum et al. | |
| 9,820,863 B2 * | 11/2017 | Guizzardi | A61F 2/442 |
| 2003/0078668 A1 | 4/2003 | Michelson | |
| 2003/0191533 A1 * | 10/2003 | Dixon | A61F 2/30767 |
| | | | 623/17.14 |
| 2004/0176844 A1 * | 9/2004 | Zubok | A61F 2/442 |
| | | | 623/23.39 |
| 2004/0243241 A1 * | 12/2004 | Istephanous | A61L 31/124 |
| | | | 606/76 |
| 2006/0190082 A1 | 8/2006 | Keller et al. | |
| 2007/0112428 A1 | 5/2007 | Lancial | |
| 2008/0300685 A1 | 12/2008 | Carls et al. | |
| 2010/0137992 A1 | 6/2010 | Buttner-Janz et al. | |
| 2012/0083891 A1 | 4/2012 | Keller | |

\* cited by examiner

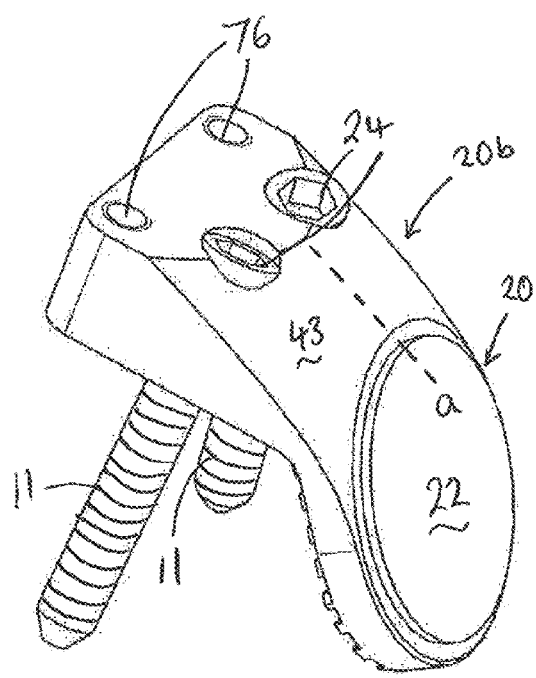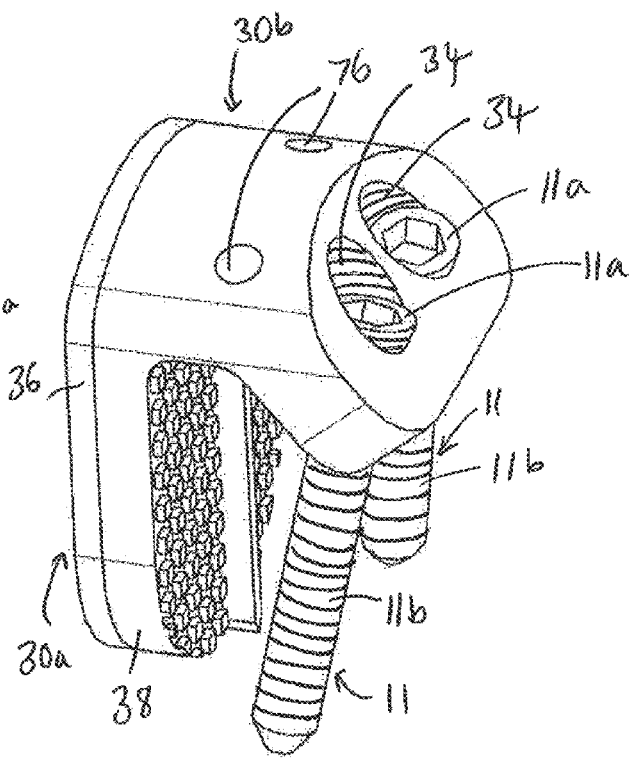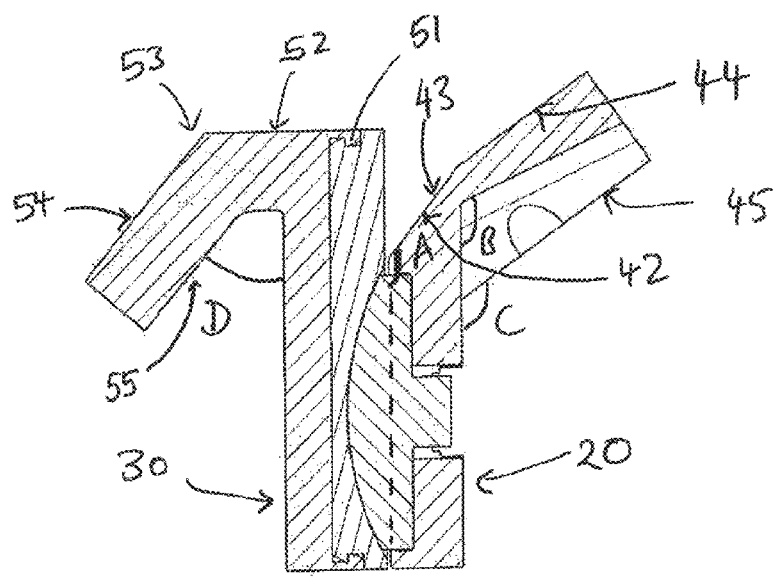
Fig. 3A
Fig. 3B
Fig. 4

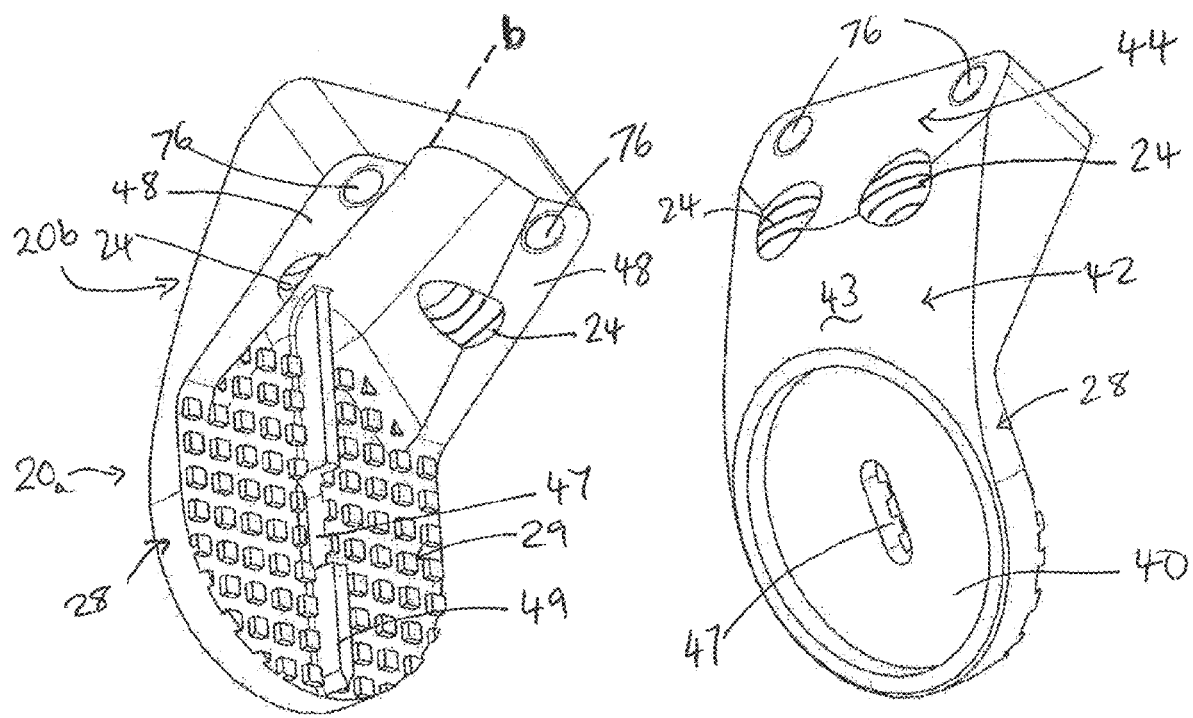
FIG. 5A
FIG. 5B
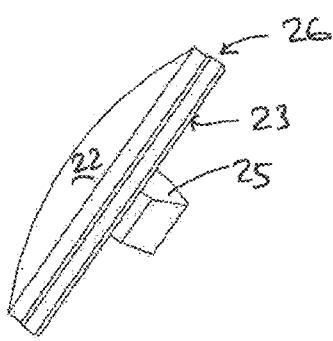
FIG. 5C
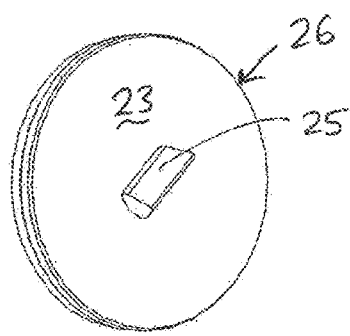
FIG. 5D

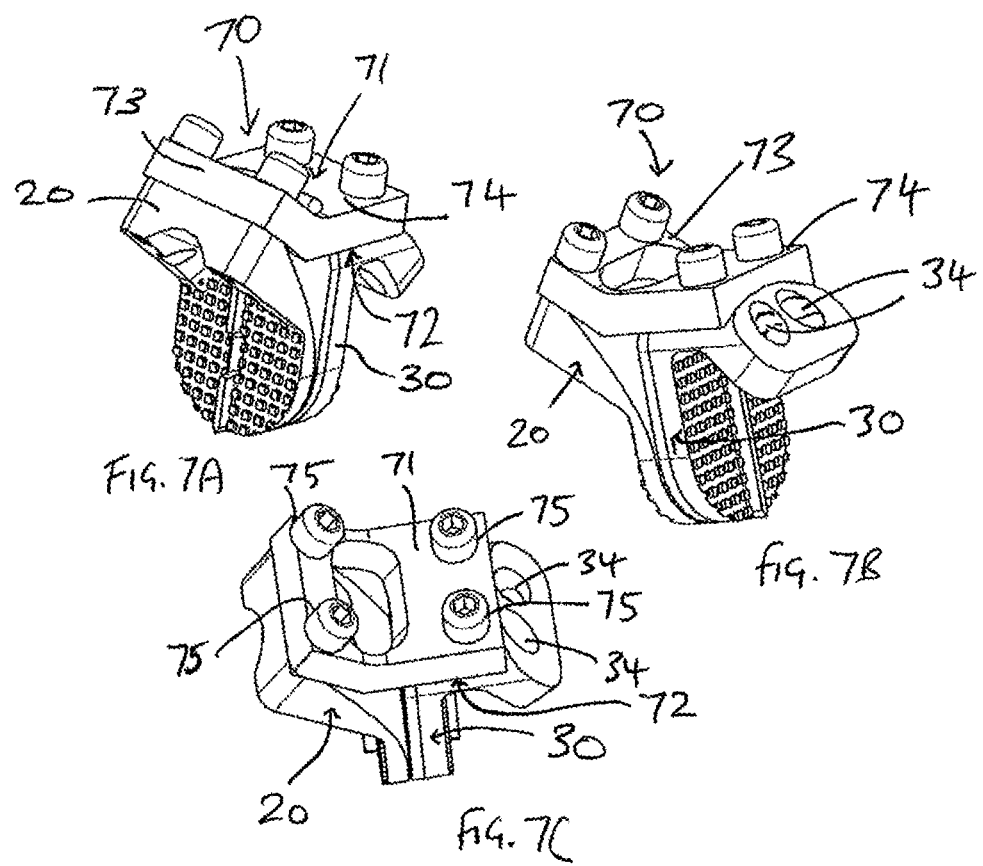

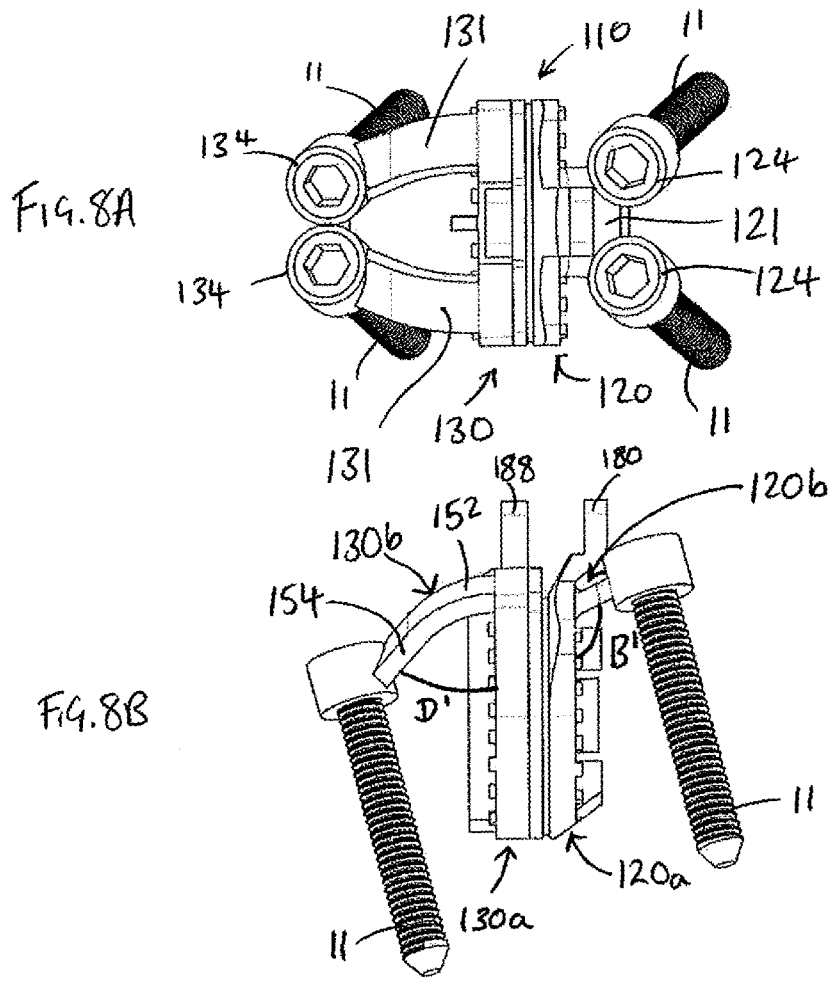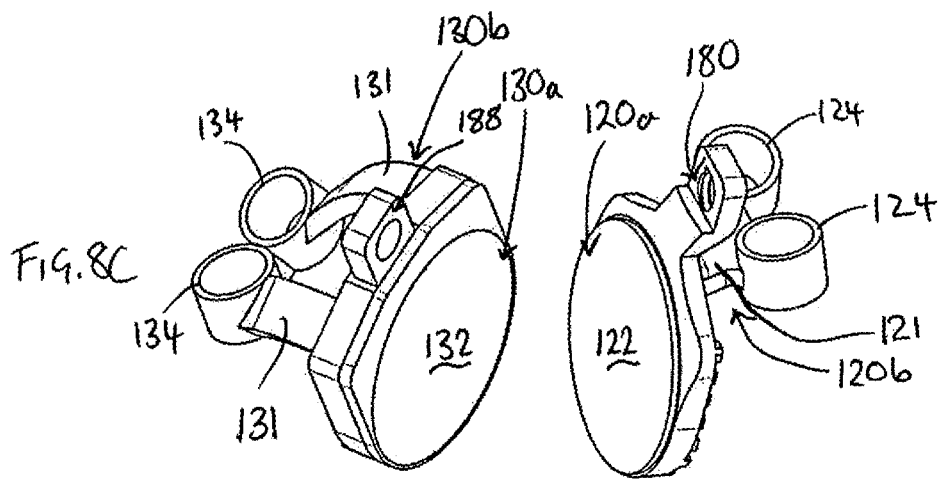

METHOD OF MAKING A PROSTHETIC INTERVERTEBRAL DISC JOINT ASSEMBLY

CROSS REFERENCE TO RELATED APPLICATIONS

This application is a continuation of pending U.S. patent application Ser. No. 17/353,915, filed Jun. 22, 2021, which is a continuation of abandoned U.S. patent application Ser. No. 15/513,689 filed Mar. 23, 2017; which is a 371 of International Application PCT/GB2015/052776, filed Sep. 24, 2015, which international application was published on Mar. 31, 2016 as International Publication WO 2016/046562 A1. The International Application claims priority to Great Britain Patent Application 1416867.8 filed Sep. 24, 2014.

FIELD OF THE INVENTION

The invention relates to an intervertebral joint implant assembly for replacing at least a portion of an intervertebral disc between first and second adjacent vertebrae in a subject's spinal column. The implant assembly provides an intervertebral joint replacement prosthesis, and in particular the invention is directed to replacement of the intervertebral joint in the cervical region of the spine.

BACKGROUND TO THE INVENTION

The spine or vertebral column comprises a plurality of separate vertebrae. The vertebrae are movable relative to one another, and separated from one another by intervertebral discs. The intervertebral discs are shock-absorbing, fibro-cartilaginous joints between adjacent vertebrae.

In its entirety, the spinal column is highly complex in that it houses and protects critical elements of the nervous system which have innumerable peripheral nerves and arterial and venous bodies in close proximity. In spite of these complexities, the spine is a highly flexible structure, capable of a high degree of curvature and twist through a wide range of motion. Between each adjacent pair of vertebra in the spine is an intervertebral disc, which together with two facet joints, laterally one on either side of the intervertebral disc, provide motion in six degrees of freedom.

Degeneration of an intervertebral disc can lead to alteration in the transfer of loads in the spine, leading to severe pain. One option for treating a subject with disc degeneration is fusion of the intervertebral joint in question. However, in fusing adjacent vertebrae together, motion at that point is prevented and fusion can lead to higher strain being experienced in the region of the spine near the fused vertebrae, causing further disc degeneration between other nearby vertebrae.

An alternative to fusion for the treatment of disc degeneration is disc replacement with a disc replacement prosthesis. This procedure aims to provide motion at the prosthesis site. Although some disc replacement prostheses have been devised for use in humans, little work has been done on treating disc degeneration in non-human mammals such as dogs. Dogs commonly suffer disc degeneration and a disc replacement prosthesis that is suitable for use in non-human mammals such as dogs would be beneficial.

SUMMARY OF INVENTION

According to a first aspect of the invention there is provided a prosthetic intervertebral disc joint assembly for replacing at least a portion of an intervertebral disc between first and second adjacent vertebrae, each vertebra having an anterior side and a posterior side, the assembly having a leading end which leads as the assembly is inserted into the intervertebral space and a trailing end opposite the leading end, and an intervertebral plane passing therebetween which substantially aligns with the intervertebral plane between the adjacent vertebrae when installed, the assembly comprising:
a first component for engaging a first vertebra, the first component having an intervertebral portion insertable between adjacent vertebrae and having a bone-engaging side for engaging an endplate of the first vertebra and an inner side opposite the bone-engaging side, the intervertebral portion of the first component further having a leading end and a trailing end, the inner side of the intervertebral portion of the first component having an articulating surface comprising a generally convex surface;
a second component for engaging a second vertebra, the second component having an intervertebral portion insertable between adjacent vertebrae and having a bone-engaging side for engaging an endplate of the second vertebra and an inner side opposite the bone-engaging side, the intervertebral portion of the second component further having a leading end and a trailing end, the inner side of the intervertebral portion of the second component having an articulating surface comprising a generally concave surface;
wherein the convex articulating surface of the first component is sized and shaped to pivot in the concave articulating surface of the second component, and
wherein the first component further comprises a fixation portion for securing the first component to the anterior side of the first vertebra, said fixation portion extending from the trailing end of the intervertebral portion of the first component and wherein the second component further comprises a fixation portion for securing the second component to the anterior side of the second vertebra, said fixation portion extending from the trailing end of the intervertebral portion of the second component.

The inventors have realized that by providing a fixation portion on each of the first and second components to secure the first and second components to the anterior side of respective first and second vertebrae, this allows the implant assembly to be stably secured to the vertebrae as soon as the implant assembly has been implanted. Intervertebral disc replacements of the prior art have typically included means for fixing the intervertebral components to the adjacent vertebrae via bone ingrowth, for example via bone ingrowth into porous surfaces on the bone-facing side of the intervertebral components. In such implants, surface treatment to encourage bone ingrowth is the only means for fixing the component to the adjacent vertebra. However, such means for securing an implant assembly would not be suitable for use in animal subjects as once such an assembly is installed, the subject must rest the joint for a period after surgery to allow for ingrowth of bone into the prosthesis, to stabilize the prosthesis. Human subjects can be taught how to control their post-operative activities to avoid extremes of flexion/extension of the intervertebral joint etc. whilst bone is ingrowing into the implanted components. However, non-human subjects do not have the ability to understand and comply with restrictions to movement that a human might receive from a physician after surgery. Although attempts can be made to restrict an animal subject from making extreme movements, often the animal will overcome restraints that might be used post-operatively, therefore it can be difficult to restrict an animal subject from making extreme movements. Therefore having fixation portions on the components of the implant assembly to secure the components to the anterior sides of the adjacent vertebrae provides stable anchoring of the implant assembly, straight after surgery. Whereas it might be thought that using anterior flanges to secure intervertebral components to vertebrae might restrict joint movement, restricting the maximum amount of flexion provided by the prosthetic joint for example, the inventors have realized that the fixation portion on each of the first and second components can be configured so as not to restrict flexion unduly. The present invention is therefore particularly suitable for non-human mammals, such as canine subjects.

The fixation portion of each component is preferably integral with the body of the respective component. The fixation portion of each component extends generally away from a trailing part of the articulating surface of the corresponding component. When the intervertebral implant assembly is implanted between adjacent vertebrae, the first and second components remain operably engaged with one another without a locking mechanism.

Suitably the convex articulating surface of the first component protrudes away from the intervertebral plane passing through the body of the first component, such that the convex articulating surface protrudes like a domed area protruding from the remainder of the first component.

The term vertebral endplates refers to the top and bottom portions of the vertebral bodies that interface with the intervertebral discs.

The term subject as used herein can be a human or animal subject.

The terms lateral, anterior, posterior, ventral, dorsal, cranial, caudal, sagittal etc. as used herein have the usual meanings in relation to anatomy. Anatomical directional terms used herein in relation to the assembly or components of the assembly refer to anatomical planes/axes of the assembly when the assembly or components of the assembly is/are installed in a subject. It will be understood that components of the invention can be positioned in a number of different orientations when outside of the subject, the directional terminology being used for purposes of illustration.

As used herein, the term distal or distally refers to location away from the point of attachment/connection of the corresponding piece with the remainder of the component or assembly. As used herein, the term proximal or proximally refers to a location towards the point of attachment/connection of the corresponding piece with the remainder of the component or assembly.

Preferably the generally convex articulating surface of the first component is substantially spherically curved. The convex articulating surface may be non-spherical however, and can have an ellipsoidal surface for example.

Preferably the generally concave articulating surface of the second component is substantially spherically curved. The concave articulating surface may be non-spherical however, and can have an ellipsoidal surface for example.

Preferably the generally convex articulating surface of the first component is substantially spherically curved and the generally concave articulating surface of the second component is correspondingly substantially spherically curved to match the curvature of the articulating surface of the first component.

Preferably the fixation portion of the first component has a bone-engaging side presenting towards the first vertebra when implanted and an outer side opposite the bone-engaging side, at least part of the outer side of the fixation portion of the first component being substantially aligned with or substantially within a notional arc the perimeter of which aligns with the convex articulating surface of the first component in the sagittal plane, such that said at least part of the fixation portion of the first component does not impinge against the second component during flexion of the intervertebral disc joint assembly in use. In particular, by means of this configuration, said at least part of the fixation portion of the first component does not impinge against the edge of the concave articulating surface of the second component or against the fixation portion of the second component. In other words, due to the configuration of the first component, said at least part of the fixation portion of the first component does not strike or collide with the second component during flexion (although said at least part of the fixation portion of the first component may touch the concave articulating surface of the second component in flexion). Where the convex articulating surface has a constant radius of curvature in the sagittal plane, said notional arc will be an arc of a notional circle. Where the convex articulating surface is parabolically curved in the sagittal plane, said notional arc will be an arc of a notional ellipse. Where the convex articulating surface is spherically curved, preferably said at least part of the outer side of the fixation portion of the first component is substantially aligned with or substantially within a notional sphere the perimeter of which aligns with the convex articulating surface of the first component. Said at least part of the fixation portion of the first component which is substantially aligned with or substantially within said notional arc is said at least part of the fixation portion which extends directly from the convex articulating surface of the first component. By shaping the first component in this way said at least part of the fixation portion of the first component will not impinge against the second component during flexion. This shape can be achieved for example by providing said at least part of the fixation portion which is positioned directly anteriorly to the convex articulating surface with a chamfered profile in the sagittal plane, thus providing a configuration which allows for a natural range of flexion at the joint whilst minimizing the need or preventing the need to remove vertebral bone from the first vertebra before the first component is installed.

Preferably the fixation portion of the first component has a proximal portion proximal to the intervertebral portion of the first component, the proximal portion of the first component having an outer side at least part of which presents towards the second component when the assembly is implanted, at least part of the outer side of the proximal portion of the first component being aligned with or substantially within a notional arc, the perimeter of which aligns with the convex articulating surface of the first component in the sagittal plane, such that said at least part of the proximal portion of the first component does not impinge against the second component during flexion of the intervertebral disc joint assembly in use.

The intervertebral plane can have a different orientation with respect to the longitudinal axis of the spine in four legged animals such as dogs than it does in humans. In the cervical region of a dog's spine for example, the intervertebral plane between adjacent vertebrae may be non-perpendicular to the longitudinal axis of the spine. Therefore disc joint replacement assemblies for humans may not be suitable for use in four legged animals for example. Whereas it might be thought that using anterior flanges to secure intervertebral components to vertebrae wherein the intervertebral plane is non-orthogonal to the longitudinal axis of the spine could restrict the maximum amount of flexion that can be provided by the prosthetic joint due to impingement of the anterior flange of the domed component with that of the concave component, the inventors have realized that the fixation portion of each of the first and second components can be shaped so as to allow for a natural range of flexion at the joint. The fixation portion on the component which engages with the vertebra on the caudal side can also be shaped so as to allow it to sit stably on the bone whilst minimizing the need or preventing the need to remove vertebral bone to ensure stable seating.

Preferably the first component has a projection extending from the trailing end of the intervertebral portion of the first component, and wherein the second component has a projection extending from the trailing end of the intervertebral portion of the second component, said projections being adapted to be coupled together during installation of the assembly into an intervertebral space of a subject. The projections can suitably be used to couple the first and second components together so that the first and second components can be held together in a fixed orientation relative to one another for ease of installation.

Preferably the projection of the first component has a first side which presents towards the second component when the assembly is implanted, at least part of the first side being substantially aligned with or substantially within a notional arc the perimeter of which aligns with the convex articulating surface of the first component in the sagittal plane, such that said at least part of the first side of the projection of the first component does not impinge against the second component during flexion of the intervertebral disc joint assembly in use.

Preferably the projection of the first component has a proximal portion proximal to the intervertebral portion of the first component, the proximal portion of the projection of the first component having a first side which presents towards the second component when the assembly is implanted, at least part of the first side of the proximal portion of the projection of the first component being aligned with or substantially within a notional arc, the perimeter of which aligns with the convex articulating surface of the first component in the sagittal plane, such that said at least part of the proximal portion of the projection does not impinge against the second component during flexion of the intervertebral disc joint assembly in use.

Preferably the projection of the first component has a distal portion which extends substantially parallel with an intervertebral plane passing through the intervertebral portion of the first component. The proximal portion of the projection is preferably between the distal portion of the projection and the intervertebral portion of the first component. The proximal portion of the projection of the first component is preferably angled relative to the intervertebral plane of the first component and the distal portion of the projection is substantially parallel to the intervertebral plane, providing a projection with a stepped profile.

Preferably the projection of the second component extends substantially parallel with an intervertebral plane passing through the intervertebral portion of the second component.

Preferably the projections of the first and second components each include a hole for receiving a fixing for coupling the first and second components together. The hole in the projection of the first component is preferably in the distal portion of the projection. The holes in the projections of the first and second components are preferably collinear when the first and second components are assembled together with the intervertebral plane of the first component substantially parallel with the intervertebral plane of the second component.

Preferably at least one of the holes in the projections of the first and second components is at least partially internally threaded for receiving a threaded fixing for coupling the first and second components together. The first and second components can therefore be releasably clamped together during installation.

Preferably the assembly further comprises a spacer adapted to be receivable between the projection of the first component and the projection of the second component. The spacer preferably has a through bore for receiving a fixing therein for coupling the first and second components together. The spacer preferably includes first and second recesses, the first recess for receiving the projection of the first component when assembled and the second recess for receiving the projection of the second component when assembled. The projection of the first component preferably has a shoulder between the proximal portion and the distal portion of the projection against which the spacer seats when assembled.

Preferably the fixation portion of the first component and/or the fixation portion of the second component are bendable. This allows for adjustment of the angle of the bone screws to be received by the fixation portion relative to the intervertebral plane. This assists during installation in that the fixation portions can be bent by the surgeon to optimize placement of the bone screw or bone screws assembled to it into stable anchoring positions in the bone. The fixation portions are preferably bendable about an axis which is substantially parallel to the medio-lateral axis.

Preferably each fixation portion comprises at least one arm. One or each fixation portion of the first and second components may comprise two arms. Each at least one arm of the respective fixation portion preferably extends away from the respective component. The fixation portion of the first component preferably comprises an arm having first and second through holes at or near its distal end for receiving bone screws. The fixation portion of the second component preferably comprises first and second arms, each having a through hole at or near its distal end for receiving a bone screw. The distal ends of the first and second arms of the fixation portion of the second component are preferably joined to one another. The portions of each arm between the distal end and the proximal end which extends from the second component can be manipulated independently of one another so as to align the arms independently, depending on the underlying bony anatomy that they are to bridge over.

Preferably each fixation portion has at least one through hole for receiving a bone screw. Each fixation portion preferably includes first and second through holes, each for receiving a bone screw.

Preferably said at least one through hole is at least partially internally threaded for receiving a bone screw therein with a correspondingly externally threaded head. Said at least one through hole may receive a locking head screw with externally threaded head, so that the alignment of the screw with reference to the fixation portion is fixed, therefore providing strong anchorage to the bone.

Preferably each fixation portion has first and second through holes each through hole having a longitudinal axis, the longitudinal axis of each through hole being angled at a predetermined angle relative to the fixation portion such that first and second bone screws will diverge from one another when installed in the first and second through holes.

Preferably the fixation portion of the first component is angled relative to an intervertebral plane passing through the intervertebral portion of the first component and the fixation portion of the second component is angled relative to an intervertebral plane passing through the intervertebral portion of the second component.

Preferably the included angle between at least part of the fixation portion of the first component and an intervertebral plane passing through the intervertebral portion of the first component is an obtuse angle. In other words, the included angle between at least part of the fixation portion and the plane of the bone-engaging side of the intervertebral portion is an obtuse angle.

Preferably the outer side of the proximal portion of the fixation portion of the first component is at least partially convexly curved. Suitably at least part of said convexly curved surface is frustoconical. Preferably said outer side is at least partially parabolically curved in cross-section, the parabolically curved outer side having a longitudinal crest.

Preferably the included angle A in the sagittal plane between a longitudinal axis of the crest of the parabolically curved outer side of the proximal portion of the fixation portion of the first component and an intervertebral plane passing through the intervertebral portion of the first component is between about 135° and 145°.

Preferably the fixation portion of the first component has a bone-engaging side presenting towards the first vertebra when implanted, the bone-engaging side of the fixation portion being concavely curved. Preferably said bone-engaging side is parabolically curved in cross-section, the parabolically curved bone-engaging side having a longitudinal trough. The bone-engaging side is configured to seat stably on longitudinal ridge on anterior side of the first vertebra.

Preferably the included angle B in the sagittal plane between a longitudinal axis of the trough of the parabolically curved bone-engaging side and an intervertebral plane passing through the intervertebral portion of the first component is between about 105° and 125°.

Preferably said parabolically curved bone-engaging side of the fixation portion of the first component has lateral side edges configured to engage the anterior side of the first vertebra when installed, the included angle C in the sagittal plane between the lateral side edges and an intervertebral plane passing through the intervertebral portion of the first component being between about 115° and 135°.

Preferably the included angle between at least part of the fixation portion of the second component and an intervertebral plane passing through the intervertebral portion of the second component is an acute angle.

Preferably the fixation portion of the second component has a proximal portion proximal to the intervertebral portion and a distal portion distal of the intervertebral portion, the included angle D between the distal portion and an intervertebral plane passing through the intervertebral portion of the second component being an acute angle. Preferably said acute angle is between about 30° and 50°.

Preferably said proximal portion of the fixation portion of the second component extends substantially orthogonally to an intervertebral plane passing through the intervertebral portion of the second component.

Preferably the articulating surface of the first component has a radius of curvature of between about 10 and 25 mm. The articulating surface of the second component has a corresponding radius of curvature which substantially matches that of the articulating surface of the first component.

Preferably the radius of curvature of the articulating surface of the first component is predetermined to substantially match that of the subject's natural radius of curvature at the intervertebral disc joint, at least in the sagittal plane.

As well as the intervertebral disc joint, each adjacent pair of vertebrae in the spine is united by a pair of facet joints. The facet joints guide the type of movement that can occur at the particular spinal motion segment. The radius of curvature of the articulating surface of the present intervertebral disc joint implant assembly is predetermined to closely match that of the natural intervertebral disc joint so as to provide the facet joints either side of the artificial disc with their natural range of motion as if the intervertebral disc were healthy and intact.

If the subject is a non-human mammal such as a dog, the radius of curvature of the prosthetic articulating surfaces can be predetermined or selected from a plurality of components with different radii of curvature to match or nearly match the natural radius of curvature at the joint in the subject that the assembly is being installed at. The radius of curvature of the articulating surfaces is predetermined to be within 10 mm, preferably 5 mm, even more preferably 3 mm, 2 mm or 1.5 mm of the subject's natural radius of curvature at the intervertebral disc joint.

Preferably the radius of curvature of the articulating surface of the first component, at least in the sagittal plane, is predetermined such that once the prosthetic intervertebral disc joint assembly is installed, a common centre of rotation for flexion/extension is provided for the articulating surfaces of the prosthetic intervertebral disc joint assembly and for each of the articulating surfaces of the two facet joints between said first and second vertebrae.

Preferably the first component comprises a bearing insert and a supporting body, the bearing insert having the articulating surface thereon and being received, when assembled, in a recess in the supporting body. Preferably the bearing insert of the first component is made from cobalt chrome. Preferably the supporting body of the first component is made from titanium or titanium alloy. Preferably the bearing insert is coupleable to the supporting body of the first component via an interference fit. Preferably the bearing insert comprises a circular bearing portion receivable in a corresponding circular recess in the supporting body of the first component. Preferably the bearing insert of the first component has a bearing surface and a back surface and the bearing insert further comprises a protrusion extending from the back surface which is receiveable in an aperture in the supporting body of the first component.

Preferably the second component comprises a bearing insert and a supporting body, the bearing insert having the articulating surface thereon and being received, when assembled, in a recess in the supporting body. Preferably the bearing insert of the second component is made from a polymeric material. Preferably the bearing insert of the second component is made from polyether ether ketone (PEEK). Preferably the supporting body of the second component is made from titanium or titanium alloy. Preferably the bearing insert is coupleable to the supporting body of the second component via a snap fit.

Preferably the bearing insert comprises is generally oblong shaped and is receivable in a correspondingly shaped recess in the supporting body of the second component. The insert is generally oblong in shape in that it is longer than it is wide.

Preferably the first component is a caudal component for engaging a vertebra of an adjacent vertebrae pair on the caudal side of the intervertebral disc space and the second component is a cranial component for engaging a vertebra of an adjacent vertebrae pair on the cranial side of the intervertebral disc space.

According to a further aspect of the invention there is provided a kit for assembly into a prosthetic intervertebral disc joint assembly as described above, wherein the kit comprises the parts of the assembly according as described above. Preferably the kit comprises a plurality of differently first components and second components of different sizes and/or shapes. Components that most closely match the subject's anatomy can be selected so as to assist in restoring natural joint action. Preferably the kit further comprises a clamp for holding the first and second components together during installation. The clamp is preferably releasably coupleable to the fixation portions of the first and second components. Preferably the first and second components each have at least one hole and the clamp has corresponding throughbores, the throughbores in the clamp being arranged such that a locking member is receivable through each throughbore and its corresponding hole in the first or second component to secure the clamp to the first and second components. The locking member is preferably a screw or bolt.

According to a further aspect of the invention there is provided a method of installing a prosthetic intervertebral disc joint assembly using a kit as described above, the method comprising the steps of inserting first and second components between first and second adjacent vertebrae and securing the fixation portions of the first and second components to the first and second vertebrae respectively. The method may comprise the steps of inserting first and second components between first and second adjacent vertebrae whilst the first and second components are clamped together by said clamp and securing the first and second components to the first and second vertebrae respectively.

According to a further aspect of the invention there is provided a computer-readable medium encoded with instructions for creating a prosthetic intervertebral disc joint assembly as described above including instructions for defining the parts of the assembly as described above. The computer-readable medium is preferably non-transitory.

BRIEF DESCRIPTION OF THE DRAWINGS

A preferred embodiment of the present invention will now be more particularly described by way of example only with reference to the accompanying drawings, wherein:

FIGS. 1 to 7 show views of a prosthetic intervertebral disc joint assembly according to the invention;

FIG. 3A shows the first component with bone screws received in the screw holes;

FIG. 3B shows the second component of the assembly of FIG. 1 with bone screws received in the screw holes;

FIG. 4 shows a cross-section in the sagittal plane of the first and second components assembled together;

FIG. 5A shows a rear perspective view of the supporting body of the first component;

FIG. 5B shows a front perspective view of the supporting body of the first component;

FIG. 5C shows a side perspective view of the insert of the first component;

FIG. 5D shows a rear perspective view of the insert of the first component;

FIGS. 7A and 7B shows side perspective views, one from each side, of the first and second components held together ready for installation using a clamp;

FIG. 7C shows a top perspective view of the assembly of FIGS. 7A and 7B;

FIGS. 8A to 8F are perspective views of a spinal implant assembly according to a further embodiment, FIG. 8A being an anterior view of the assembly;

FIG. 8B is a side view of the assembly;

FIG. 8C is an exploded view of the first and second components of the assembly;

FIG. 8D is a side perspective view of the assembly;

FIG. 8E is a side perspective view of the assembly with a spacer and screw for holding the spacer and the first and second components together, the screw and spacer shown exploded from the assembly;

FIG. 8F is a side perspective view of the assembly of FIG. 8E with the spacer and screw attached thereto, ready for installation;

DESCRIPTION OF THE PREFERRED EMBODIMENTS

The present embodiments represent currently the best ways known to the applicant of putting the invention into practice. But they are not the only ways in which this can be achieved. They are illustrated, and they will now be described, by way of example only.

Figure 1A:
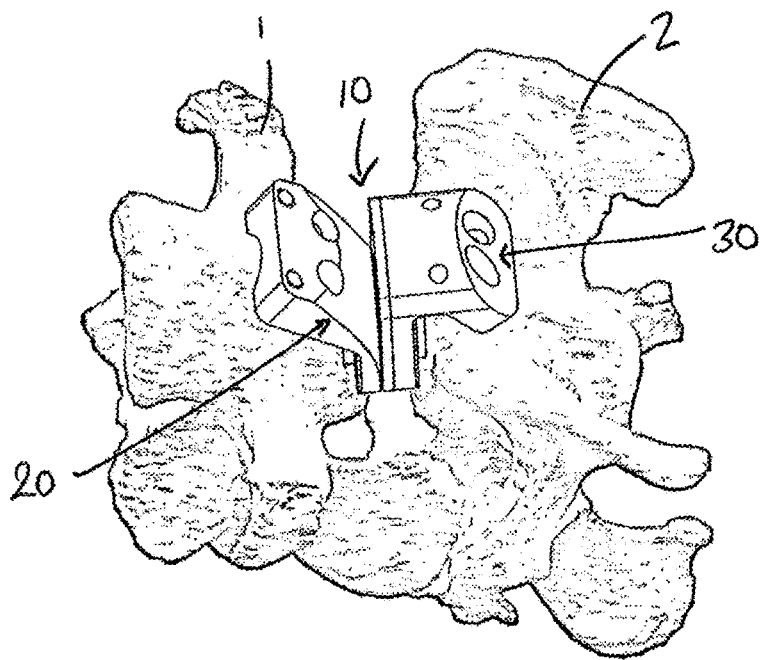
FIG. 1A shows the assembly installed in an intervertebral space but not yet secured to the vertebrae with bone screws.
Figure 2A:
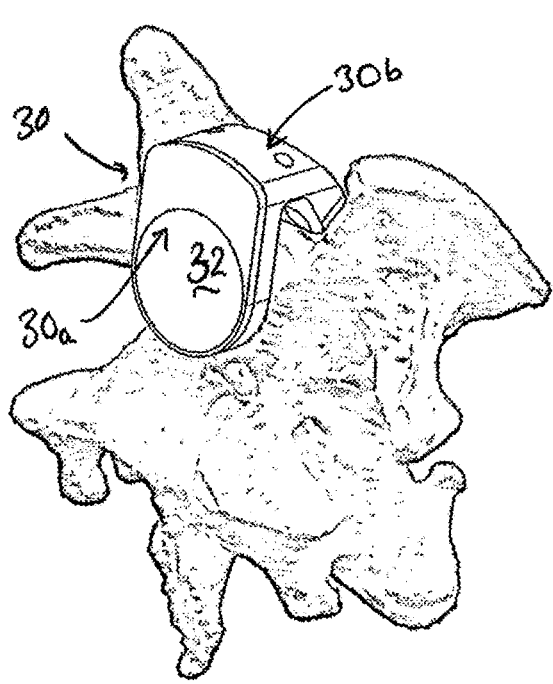
FIGS. 2A and 2B are views exploded from FIG. 1, FIG. 2A being a view of the first component of the implant assembly shown seated on a first vertebra and FIG. 2B being a view of the second component of the implant assembly shown seated on a second vertebra.
Figure 2B:
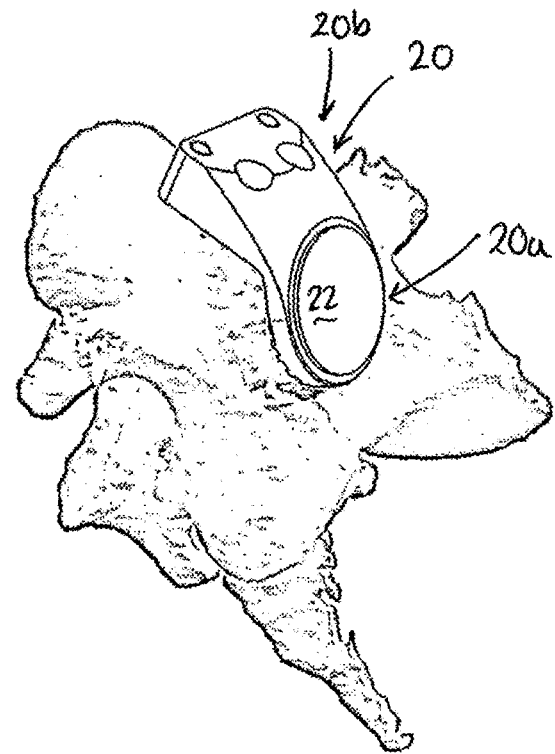

Referring to FIG. 1A, a prosthetic intervertebral disc joint assembly 10 for replacing at least a portion of an intervertebral disc between first and second adjacent vertebrae 1, 2 is shown. The assembly can be used to replace an intervertebral disc and to restore motion at the intervertebral joint. The assembly 10 comprises a first component 20 for engaging a first vertebra 1 and a second component 30 for engaging a second vertebra 2. The first component 20 is a caudal component, in that it is configured to be installed adjacent a vertebra 1 of a vertebrae pair on the caudal side of the intervertebral disc space. The second component 30 is a cranial component, in that it is configured to be installed adjacent a vertebra 2 of a vertebrae pair that is on the cranial side of the intervertebral disc space. Referring to FIGS. 2A and 2B, each of the first and second components 20, 30 has an intervertebral portion 20a, 30a for inserting in the intervertebral disc space between the vertebrae 1, 2 and a fixation portion 20b, 30b, extending from the corresponding intervertebral portion 20a, 30a, for securing the component 20, 30 to the anterior side of the adjacent vertebra 1, 2. The implant assembly has a leading end which leads as the implant assembly is inserted into the intervertebral space and a trailing end opposite the leading end, an intervertebral plane passing therebetween which substantially aligns with the intervertebral plane between the adjacent vertebrae when installed. The fixation portion 20b of the first component 20 is angled relative to the intervertebral plane passing through the intervertebral portion 20a. Similarly the fixation portion 30b of the second component 30 is angled relative to the intervertebral plane passing through the intervertebral portion 30a.

The intervertebral portion of the first component 20 has a generally convex articulating surface 22, shaped and sized to articulate with a correspondingly concavely curved articulating surface 32 of the intervertebral portion 30a of the second component 30. The articulating surfaces 22, 32 are spherically curved in this embodiment, providing a ball-and-socket type articulating assembly, however the articulating surfaces may have other shapes, such as to provide a ball-and-trough type articulating assembly for example. The convex and concave articulating surfaces 22, 32 of the first and second components are interengageable such that the first and second components can pivot with respect to one another when the implant assembly is installed. When installed, the implant assembly can restore movement at the intervertebral disc joint, namely flexion/extension, lateral bending and axial rotation. The present implant assembly is particularly suited for implantation in non-human mammals, such as dogs, via an anterior (ventral) approach. The present assembly is particularly suited for implantation in the cervical region of the spine.

Figure 1B:
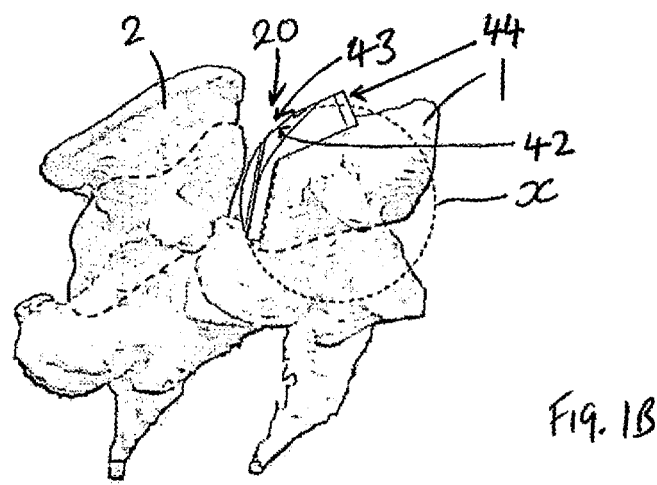
FIG. 1B shows only the first component installed in an intervertebral space, for reference purposes.

The radius of curvature of the convex and concave articulating surfaces 22, 32 closely matches, within about 5 mm, preferably about 3 mm or 2 mm, and ideally about 1.5 mm, the natural radius of curvature at the intervertebral disc joint. In the present embodiment, the radius of curvature of the articulating surfaces is 19 mm. The radius of curvature of the articulating surfaces 22, 32 can be predetermined to closely match that of the natural intervertebral joint the assembly is to be installed at, and the radius of curvature will typically be chosen to be in the range of about 10 to 25 mm depending on the size or breed of subject (for example when used in dogs). A set comprising a plurality of implant assembly components can be provided with differing, discrete dimensions within a particular range, such as with articulating surfaces 22, 32 with differing radii of curvature, and the components with the radius of curvature closest to the natural radius of curvature for the subject can be selected from the set for implantation. Referring to FIG. 1B, the radius of curvature of the articulating surface in the sagittal plane is large enough such that a common centre of rotation is provided for flexion/extension at the prosthetic intervertebral joint and at each of the facet joints. This provides three areas of bearing contact during flexion/extension between the first and second vertebrae. Therefore, the radius of curvature in the sagittal plane is determined such that all three pairs of articulating surfaces (namely the prosthetic intervertebral articulating surfaces 22, 32 and the articular surfaces of each facet joint) maintain contact during the full range of flexion/extension. The articulating surface 22 is therefore shaped such that the centre of rotation in the sagittal plane is located, when installed, at a point which allows for the three areas of bearing contact to be maintained during flexion/extension.

Figure 1C:
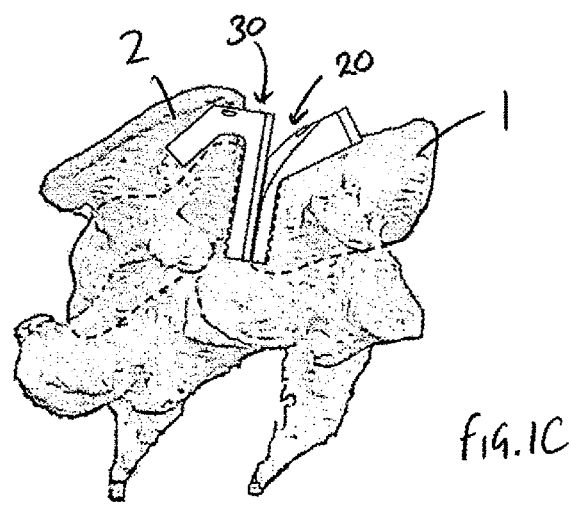
FIGS. 1C shows a side view of the first and second components installed in an intervertebral space.

The fixation portions 20b, 30b of the first and second components 20, 30 each include at least one through hole 24, 34 for receiving a bone screw 11 (bone screws are shown in FIGS. 3A and 3B, but not shown in FIGS. 1, 2A and 2B). In the particular embodiment shown in the figures, the fixation portion 20b of the first component 20 has first and second through holes 24 and the fixation portion 30b of the second component 30 has first and second through holes 34, each through hole receiving a bone screw 11 in use. Each bone screw has a head portion 11a and a shank portion 11b. The shank portion 11b of each bone screw is externally threaded to secure into vertebral bone. The head portion 11a of each bone screw is also externally threaded. The external threading of the head portion 11a of each bone screw corresponds with internal threading of the corresponding through hole 24, 34 that the bone screw is received in such that each bone screw 11 can be rigidly fixed relative to the corresponding component 20, 30 when installed. In alternative embodiments, the bone screws may not be threadedly fastenable to the corresponding component 20, 30. The longitudinal axis of each through hole 24, 34 is inclined at a predetermined angle relative to the corresponding component 20, 30 such that when installed, the screw 11 extends at a predetermined angle relative to the component 20, 30 it is installed in. In the particular embodiment shown in the figures, the inclines of the bores 24, 34 have been predetermined so that the screws 11 in each pair of first and second bone screws diverge from one another once installed. Components 20, 30 can be provided with different spacings between the first and second through holes 24, 34 in each component and provided with throughholes 24, 34 that have different inclines relative to the fixation portion of the component, so as to suit different vertebral bone geometry in different breeds/sizes of animal.

Referring to FIGS. 5A to 5D, the first component 20 comprises a bearing insert 26 and a supporting body 28, the insert 26 having the convex articulating surface 22 thereon and the insert 26 being received, when assembled, in a recess 40 in the supporting body. In a preferred embodiment the insert 26 is made of cobalt chrome and the supporting body 28 is made of titanium or titanium alloy, however it will be understood that the parts can be made of other materials. Instead of providing the articulating surface 22 of the first component on an initially separate insert 26, the first component 20 may be provided as a single piece with integral articulating surface. The insert 26 is circular in shape and the recess 40 in the supporting body 28 is correspondingly circular in shape to receive the insert 26. The insert 26 and recess 40 are shaped and sized such that the insert 26 can be coupled to the supporting body 28 via an interference fit.

The circular insert 26 has a substantially spherical convex bearing surface 22, a back surface 23 opposite the bearing surface 22, and a protrusion 25 extending from the back surface 23. The protrusion 25 is received in a corresponding aperture 47 in the supporting body 28 when the insert 26 is assembled with the supporting body 28 to provide an anti-rotation feature to prevent the insert 26 from rotating in recess 40 during articulation of the prosthetic joint assembly. The protrusion 25 can be any non-circular shape, and in the embodiment shown in the figures the protrusion 25 has a rectangular base and has chamfered faces extending to an outermost ridge. In the embodiment shown in the figures aperture 47 is a through hole, although it could be a blind bore for example. In some embodiments the protrusion 25 can be designed to be bent over sideways once the protrusion 25 has been inserted through hole 47, to prevent the protrusion 25 from being withdrawn from the through hole 47 and therefore to provide anchoring of the insert 26 to the supporting body 28 in addition to or instead of the interference fit provided by recess 40.

The fixation portion 20b has an outer side 43, at least part of which presents towards the second component 30 when assembled and a bone-engaging side 45 opposite the outer side 43. The fixation portion 20b has a proximal portion 42 proximal to the intervertebral portion 20a (i.e. proximal to the insert 26) and a distal portion 44 distal of the intervertebral portion 20a. In other words, the fixation portion 20b extends from the intervertebral portion 20a, with the proximal portion 42 between the distal portion 44 and the intervertebral portion 20a. The proximal portion 42 is a part of the fixation portion which extends directly anteriorly to the convex articulating surface 22. The distal portion 44 extends distally from the proximal portion 42 (i.e. distally of a trailing edge of the proximal portion 42). In this embodiment each through hole 24 for receiving a bone screw has a portion located in the proximal portion 42 and portion located in the distal portion 44, however it will be understood that the through holes 24 could be fully located in the proximal portion 42 or distal portion 44.

Referring to FIG. 1B, the articulating surface 22 has a cross-section in a sagittal plane that forms a convex arc. It will be understood that said sagittal plane of the assembly/component is orthogonal to the intervertebral plane of the assembly. A notional circle x is shown in FIG. 1B that aligns with the convex arc of the articulating surface 22 in the sagittal plane. The outer side 43 of the proximal portion 42 of the fixation portion 20b is substantially aligned with the notional circle x the perimeter of which aligns with the convex articulating surface 22 of bearing insert 26 in the sagittal plane such that the proximal portion 42 of the fixation portion 20b does not impinge against the second component during flexion of the intervertebral joint implant assembly when installed. The convex articulating surface 22 forms part of the perimeter of the notional circle x and the proximal portion 42 is enclosed by the notional circle x. Where the convex articulating surface 22 is spherical, as in the present embodiment, the proximal portion 42 of the fixation portion 20b is substantially aligned with or is substantially within a notional sphere that aligns with the convex articulating surface 22. The convex articulating surface 22 therefore forms part of the perimeter of the notional sphere and the proximal portion is enclosed by the notional sphere.

In this embodiment, the distal portion 44 of the fixation portion 20b of the second component 20 protrudes outside of the notional circle x that passes through the convex articulating surface 22 of insert 26 in the sagittal plane, therefore the distal portion 44 will impinge on the second component 30 at the maximum level of flexion of the prosthetic joint. The first component 20 is configured such that during flexion, the outer side 43 of the fixation portion 20b does not impinge against the second component 30 until at least around 20° of flexion has been achieved from the unflexed state. In this embodiment, the first and second components may provide a total of around ±25° motion in flexion/extension (i.e. a range of 50° in total), however a range of up to ±20° should be sufficient for the joint to work normally.

The fixation portion 20b of the first component 20 is configured such that it will sit on the anterior side of the first vertebra 1 when the intervertebral portion 20a is installed in the intervertebral space without the need to cut any vertebral bone from the anterior side of first vertebra 1 away (or to minimize the amount of bone from the anterior side of first vertebra 1 that needs to be cut to allow the fixation portion 20b to stably engage with the first vertebra 1). The fixation portion 20b is therefore shaped to sit on the bone without the need to trim too much bone. Referring to FIG. 1B, with the fixation portion 20b thus configured, the distal portion 44 of the fixation portion 20b of the second component 20 protrudes outside of the notional circle x that passes through the convex articulating surface 22 of insert 26 in the sagittal plane, therefore the distal portion 44 will impinge on the second component 30 at the maximum level of flexion of the prosthetic joint, however sufficient range of motion in flexion is provided for before the maximum degree of flexion is reached due to the chamfered profile of the fixation portion 20b of the second component in the sagittal plane. It will be understood that in other embodiments there may be no part of the fixation portion 20b that protrudes from the notional circle x.

In the present embodiment the outer side 43 of the proximal portion 42 of the fixation portion 20b of the first component 20 is substantially straight in the sagittal plane, as can be seen from FIG. 4, however it will be understood that it may be convexly curved in the sagittal plane for example. Referring to FIG. 3A, the outer side 43 of the proximal portion 42 is convexly curved with a parabolic cross-section in the intervertebral plane, at least part of the outer side 43 being frustoconical. The parabolically curved outer side of the proximal portion 42 has a crest in the sagittal plane having a longitudinal axis a. Referring to FIG. 4, in the sagittal plane the included angle A between the longitudinal axis a of the crest of the parabolically curved outer side 43 of the proximal portion 42 of the fixation portion 20b and the intervertebral plane i of the first component is 142° for the present embodiment. Angle A can be predetermined, for example depending on the size or breed of subject, and is preferably within the range of about 135° to 145°. The outer side 43 of the distal portion 44 of the fixation portion 20b is planar and chamfered relative to the intervertebral plane to provide a low profile to the first component 20 when implanted.

Referring to FIG. 5A, the bone-engaging side 45 of the fixation portion 20b of the first component 20 is shaped for optimal seating on the anterior side of the first vertebra 1 (i.e. the vertebra on the caudal side of the disc space). The bone-engaging side 45 is concavely curved in the intervertebral plane to provide optimal seating over a range of bony geometries that might be present in subjects. In the embodiment shown in the figures, the bone-engaging side 45 is parabolically curved in cross-section, having a longitudinal trough with longitudinal axis b. Referring to FIG. 4, the included angle B between the longitudinal axis b of the trough of the curved bone-engaging side 45 of the fixation portion 20b and the intervertebral plane i of the first component 20 is 115°. Angle B can be predetermined depending, for example on the breed and size of subject, and is preferably within the range of about 105° to 125°. The curved bone-engaging side 45 of the fixation portion 20b has lateral side edges 48. The lateral side edges 48 preferably engage the anterior side of the first vertebra 1 when the first component 20 is installed. Referring to FIG. 4, the included angle C between the lateral side edges 48 and the intervertebral plane i of the first component 20 is 125°. Angle C can be predetermined, for example depending on the breed and size of subject, and is preferably within a range of about 115° and 135°. In alternative embodiments the bone-engaging side 45 of the fixation portion 20b of the first component 20 may be differently shaped to suit different bone geometries.

The second component 30 will now be described in more detail. Referring to FIG. 4, the fixation portion 30b of the second component 30 has a proximal portion 52 proximal to the intervertebral portion 30a and a distal portion 54 distal of the intervertebral portion 30a. In other words, the fixation portion 30b extends from the intervertebral portion 30a, with the proximal portion 52 being between the distal portion 54 and the intervertebral portion 30a. In this embodiment each of the screw holes 34 for receiving a bone screw is located in the distal portion 54, although they could be in the proximal portion 52, or span between the proximal and distal portions 52, 54. The proximal and distal portions 52, 54 of the fixation portion 30b are oriented relative to the intervertebral plane i of the component so as to allow for stable fixation to the anterior side of the second vertebra 2. The proximal portion 52 extends substantially orthogonally to an intervertebral plane i passing through the first component 30. The distal portion 54 extends from the proximal portion 52 in a retrograde sense with respect to the intervertebral portion 30a. The included angle D between the distal portion 54 and the intervertebral plane i of the first component 20 is 40°. Angle D can be predetermined, for example depending on the breed and size of subject, and is preferably within a range of about 30° and 50°. The fixation portion 30b has an outer side 53, and a bone-engaging side 55 opposite the outer side 53. The orientation of proximal and distal portions 52, 54 of the fixation portion 30b provides a space on the bone-engaging side 55 between the distal portion 54 and the intervertebral portion 30a which receives a portion of the subject's bone therein when installed. Preferably the anterior side of the subject's second vertebra 2 at the site where the implant assembly is to be installed will be shaped by cutting, in readiness to receive the fixation portion 30b of the second component 30. The outer side 53 of the fixation portion 30b is configured to have a low profile when installed. In the present embodiment the outer side 53 of the proximal portion 54 is concavely curved in the intervertebral plane, however it may be differently shaped, such as with a planar outer side 53.

Referring to FIGS. 6A to 6D, the second component 30 comprises a bearing insert 36 and a supporting body 38, the insert 36 having the concave articulating surface 32 thereon and the insert 36 being received, when assembled, in a recess 50 in the supporting body. In a preferred embodiment the insert 36 is made of a polymeric material, preferably polyether ether ketone (PEEK) and the supporting body 38 is made of titanium or titanium alloy, however it will be understood that the parts can be made of other materials. Instead of providing the articulating surface 32 of the second component on an initially separate insert 36, the second component 30 may be provided as a single piece with integral articulating surface. The insert 36 is oblong in shape and the recess 50 in the supporting body 38 is correspondingly oblong in shape to receive the insert 36.

The insert 36 and recess 50 are configured such that the insert 36 can be coupled to the supporting body 38 via a snap fit. The recess 50 has an inwardly directed lip 51 extending around all or at least part of its perimeter. The insert 36 has a recessed area 56 around its periphery to receive the lip 51 therein. In the present embodiment the insert 36 has a back portion 33 opposite the concave bearing surface 32, the back portion 33 extending beyond the recessed area 56 at the leading and trailing end of the insert 56. The insert 36 can be assembled to the supporting body 38 by inserting the leading end of back portion 33 in the recess 50 in the supporting body 38, with the leading end of the back portion 33 located behind the lip 51, and then by snap fitting the trailing end of the back portion 33 behind lip 51 of the recess 50. The PEEK insert 36 is flexible enough to allow the insert 36 to be secured via a snap fit with the supporting body 38 whilst also providing a strong bearing surface.

Figure 6A:
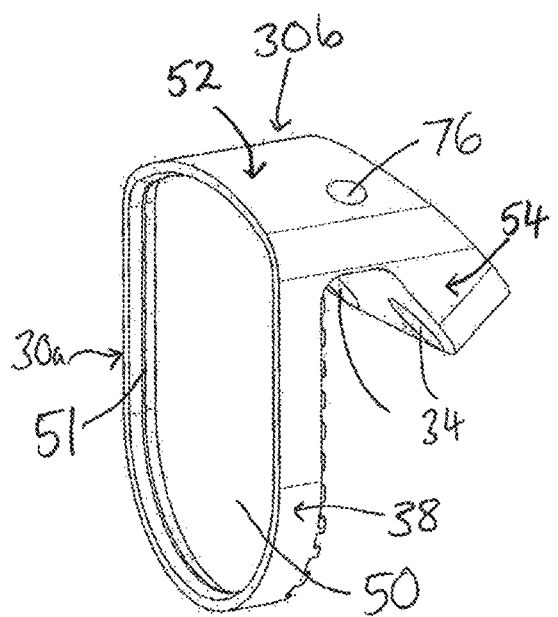
FIG. 6A shows a side perspective view of the supporting body of the second component.
Figure 6B:
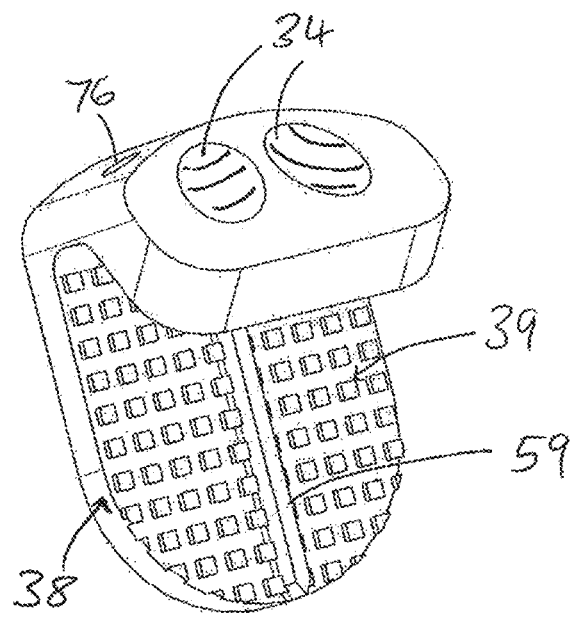
FIG. 6B shows a rear perspective view of the supporting body of the second component.
Figure 6C:
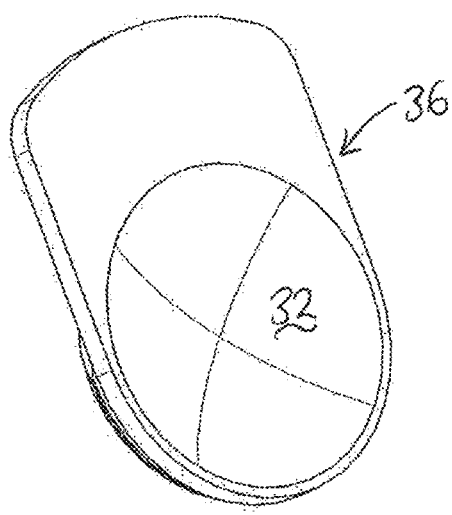
FIG. 6C shows a front perspective view of the insert of the second component.
Figure 6D:
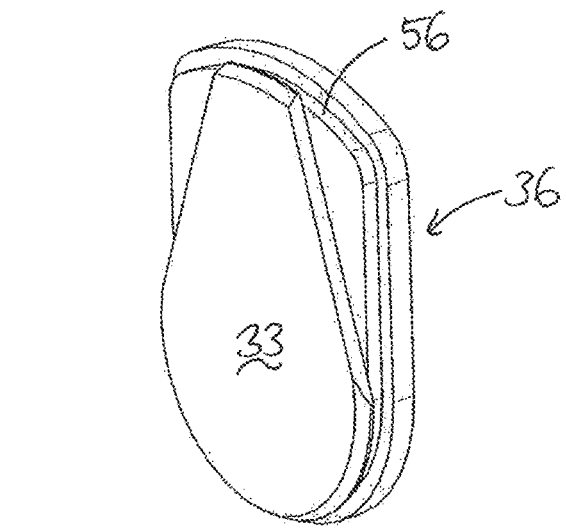
FIG. 6D shows a side perspective view of the insert of the second component.

The first and second components 20, 30 each have a bone-engaging sides 29, 39 opposite the articulating bearing surface 22, 32. Referring to FIGS. 5A and 6B, the bone-engaging sides 29, 39 of the first and second components are each stippled and hydroxyapatite coated to encourage integration with the vertebral end-plates that the bone-engaging sides 29, 39 will engage with when installed. Other treatments can be provided to the bone-engaging sides 29, 39 to encourage bone integration, such as a porous surface treatment. Each bone-engaging side 29, 39 also has an elongate fin 49, 59 protruding therefrom with a longitudinal axis aligned with an axis running from the leading end to the trailing end of the component. The fins 49, 59 further help to secure the components 20, 30 to the respective first and second vertebral end plates.

The implant assembly can be provided with a clamp 70, as shown in FIGS. 7A-7C, for holding the first and second components 20, 30 together during installation. The clamp 70 comprises an angled plate having an outer surface 71 and an implant-engaging surface 72. The implant-engaging surface 72 is configured to seat stably on the fixation portions 20b, 30b of the first and second components. The clamp 70 has a caudal portion 73 that is planar and configured to sit on the distal portion 44 of the fixation portion 20b of the first component. The clamp also has a cranial portion 74 that has a concavely curved implant-engaging surface 72 and is configured to sit on the proximal portion 52 of the fixation portion 30b of the second component. The clamp may have any suitable means for securing the clamp 70 to the first and second components 20, 30. In the present embodiment the clamp 70 has four throughbores 75 which pass from the outer surface 71 to the implant-engaging surface 72, two in the caudal portion 73 and two in the cranial portion 74 of the clamp. The throughbores 75 are arranged to align with corresponding holes 76 on the fixation portions 20b, 30b of the first and second components 20, 30, so that a screw or bolt can be received in each throughbore 75 and aligned hole 76 to secure the clamp 70 to the components, thus releasably securing the first and second components 20, 30 together. With the first and second components 20, 30 rigidly fixed with respect to one another, this aids insertion of the first and second components 20, 30 in the intervertebral space so that the convex articulating surface 22 is correctly seated in the concave articulating surface 32 when implanted. Once the implant assembly has been inserted in the intervertebral space, the clamp 70 can be removed. In alternative embodiments the clamp 70 may have only two throughbores 76, one for securing the clamp to the first component 20, and one for securing the clamp to the second component 30.

In operation in order to install the implant assembly, firstly the intervertebral joint that the implant assembly is being installed at is prepared if necessary. For example, damaged disc tissue may be removed and vertebral bone may be cut away, for example from the vertebra 2 on the cranial side of the intervertebral joint, to shape the anterior side of the vertebra 2 to receive the fixation portion 30b of the second component 30. The implant assembly with clamp 70 secured thereto, the clamp holding the first and second components 20, 30 together, is inserted in in the intervertebral disc space. The screws or bolts that hold the clamp 70 to the first and second components 20, 30 are removed such that that clamp 70 can be detached from the assembly. The first and second components 20, 30 are then secured to the first and second vertebrae 1, 2 respectively using bone screws 11.

Figure 8D:
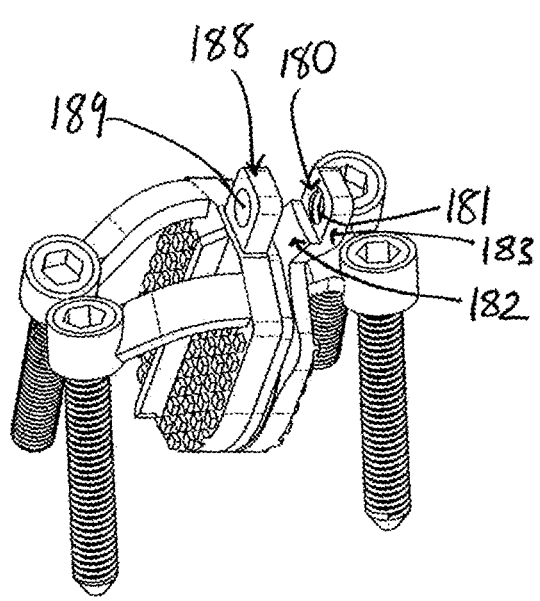
Figure 8E:
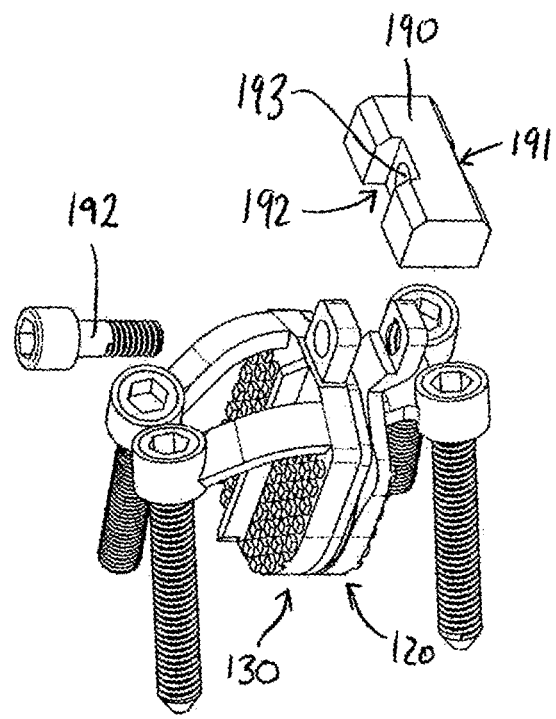

Referring to FIGS. 8A to 8G, a further embodiment of a prosthetic intervertebral disc joint assembly 110 is shown. The same reference numerals have been used in the Figures for the features of the assembly which are the same as in the embodiment of FIGS. 1 to 7. The assembly 110 comprises a first component 120 and a second component 130, the first component 120 being a caudal component and the second component 130 being a cranial component. Referring to FIG. 8C, each of the first and second components has an intervertebral portion 120a, 130a for inserting in the intervertebral disc space and a fixation portion 120b, 130b, extending from the corresponding intervertebral portion 120a, 130a, for securing the component to the anterior side of the adjacent vertebra. The intervertebral portions 120a, 130a of the FIG. 8A to 8G embodiment are very similar to those of the embodiment of FIGS. 1 to 7 whereas the fixation portions 120b, 130b differ between the embodiments and the means for clamping the components together during installation differs between the embodiments.

Like in the embodiment of FIGS. 1 to 7, in the embodiment of FIG. 8 the intervertebral portion 120a of the first component 120 has a generally convex articulating surface 122, shaped and sized to articulate with a correspondingly concavely curved articulating surface 132 of the intervertebral portion 130a of the second component 130. The articulating surfaces 22, 32 are spherically curved in this embodiment, providing a ball-and-socket type articulating assembly, however the articulating surfaces may have other shapes, such as to provide a ball-and-trough type articulating assembly for example. Preferably the intervertebral portions 120a, 130a of the first and second components have the same features as described in relation to the embodiment of FIGS. 1 to 7.

The fixation portions 120b, 130b of the first and second components comprise bendable arms 121, 131. Each arm 121, 131 is an elongate plate having an upper surface adapted to face away from the spine when installed and a lower surface opposite said upper surface. Each arm 121, 131 includes through holes 124, 134, each through hole for receiving a bone screw 11 therein. The through holes 124 may be internally threaded such that a bone screw with threaded head can be threadedly fastenable in the through hole. Alternatively, the through holes may be non-threaded. Each through hole for receiving a bone screw has a longitudinal axis which the bone screw will align to when installed in the through hole. The arms 121, 131 are preferably integral with the respective first or second component that they extend from. The arms 121, 131 are bendable such that when the intervertebral portion 120a, 130a of each component is installed in the disc space, the arms 121 and 131 can be adjusted to locate the bone screw or bone screws 11 coupled thereto at a suitable location and angle relative to the vertebra for stably securing the respective component to the bone depending on the particular bony anatomy of the subject. The arms 121, 131 are made from a suitable material that is sufficiently malleable to allow the arms 121, 131 to be bent by the surgeon during installation, whilst retaining rigidity and strength once the assembly is fully installed.

The fixation portion 120b of the first component 120 comprises a single bendable arm 121 with first and second through holes 124, each for receiving a bone screw 11, at its distal end; however, the fixation portion of the first component could instead have first and second bendable arms, each with a through hole for receiving a bone screw at the distal end, such that the angle and/or position of the first and second bone screws relative to the intervertebral portion 120a are independently adjustable. As can be seen from FIG. 8A, the longitudinal axis of the first and second through holes 124 are angled at a predetermined angle relative to the arm 121 such that the two bone screws 11 will diverge from one another when installed in the first and second through holes 124. By means of the first and second through holes 124 being located on a single bendable arm 121, the angle of inclination of the screws 11 relative to the intervertebral plane can be increased or decreased for both screws simultaneously by bending the arm 121 towards the bone or away from the bone, whilst maintaining the divergence of the first and second screws relative to one another, such that the screws avoid the spinal chord when installed.

The fixation portion 130b of the second component 130 comprises first and second bendable arms 131, each having a through hole 134 at its distal end for receiving a bone screw 11. The distal ends of the first and second arms 131 are joined to one another (i.e. the perimeter of the through holes 134 may be integral with one another at the point at which they join or they may be coupled together during manufacture, such as by welding). The first and second arms 131 are separate from one another at least at their mid-sections, therefore the separate elongate arms 131 are easy to bend during installation to achieve the desired position for the screws 11 and desired angle 11 of inclination of the screws relative to the intervertebral plane.

The longitudinal axis of the first and second through holes 134 on the second component are angled at a predetermined angle relative to one another such that the two bone screws 11 will diverge from one another when installed in the first and second through holes 134. By means of the first and second through holes 134 being joined, the angle of inclination of the screws 11 relative to the intervertebral plane can be increased or decreased for both screws simultaneously by bending the arms 131 towards the bone or away from the bone, whilst maintaining the divergence of the first and second screws relative to one another, such that the screws avoid the spinal chord when installed.

The first and second arms 131 of the second component 130 are longer than the arm 121 of the first component 120. Whilst the short length of the arm 121 of the first component 120 is suited for pivoting the through holes 124 anteriorly and posteriorly relative to the spine, so as to adjust the angle of the screws in the sagittal plane, the longer arms 131 of the second component 130 are suited for being curved so as to bridge the vertebral bone underneath whilst allowing the distal ends of screws 11 installed in the second component 130 to converge towards the intervertebral portion of the second component in the sagittal plane. Referring to FIG. 8B, typically, arm 121 will be adjusted during installation such that an included angle B' between the fixation portion 120b of the first component 120 and an intervertebral plane passing through the intervertebral portion 120a of the first component is an obtuse angle (such that the screws coupled to the first component diverge away from the intervertebral portion 120a in the sagittal plane). Typically, arms 131 will be adjusted during installation such that an included angle D' between a distal portion of the fixation portion 130b (to which the screws 11 are to be affixed) and an intervertebral plane passing through the intervertebral portion of the first component is an acute angle (such that the screws coupled to the second component converge towards the intervertebral portion 130a in the sagittal plane). The arms 131 of the second component 130 can be curved such that they each have a proximal portion 152, part of which extends substantially orthogonally to the intervertebral portion 130a or thereabouts, and a distal portion 154 that extends in a retrograde sense with respect to the intervertebral portion 130a. The orientation of the proximal and distal portions 152, 154 provides a space on the bone engaging side of the arms 131, between the distal portion 154 of the arms 131 and the intervertebral portion 130a, which receives a portion of the subject's bone therein when installed. Of course, since the arms 121, 131 are bendable, alternative configurations can be arrived at, depending on the particular subject's anatomy at the site of installation.

The implant assembly is provided with means for clamping the first and second components 120, 130 together during installation, said means being different from that of the embodiment of FIGS. 1 to 7. In the embodiment of FIGS. 8A to 8G, the first and second components 120, 130 can be clamped together using tabs or projections 180, 188 which extend from the first and second components respectively. Referring to FIG. 8D, the first component 120 has a first projection 180 extending from the trailing end of the intervertebral portion 120a and the second component 130 has a second projection 188 extending from the trailing end of the intervertebral portion 130a. Each of the projections 180, 188 has a hole therein for receiving a fixing for coupling the first and second components together during installation.

The second projection 188 comprises a planar tab which extends substantially parallel with the intervertebral plane of the second component 130 and the second projection 188 includes a through hole 189. The first projection 180 has a proximal portion 182 and a distal portion 183 which are angled relative to one another. The proximal portion 182 has a first side which presents towards the second component 130 when assembled, the first side being angled relative to the intervertebral plane. The distal portion 183 includes a through hole 181 and the distal portion 183 extends substantially parallel with the intervertebral plane of the first component 120. The assembly comprises a spacer 190 adapted to be received between the first and second projections 180, 188 and means to clamp the first and second components 120, 130 with the spacer 190 between, which in this embodiment is a screw 192, but may be other suitable means. The spacer 190 has a through hole 191 which aligns with the through holes 181 and 189 in the first and second projections 180, 188. The through hole of one of the projections is internally threaded (in this embodiment the through hole 181 in the first projection 180 is internally threaded) such that the threaded screw 192 threadedly fastens to the first projection 180. The spacer 190 has first and second recesses 191, 192, one on either side, for receiving the projections 180, 188 of the first and second components respectively when assembled. The first projection 180 has a stepped profile with a shoulder 184 between the proximal portion 182 and the distal portion 183, against which the spacer 190 seats when assembled.

Figure 8F:
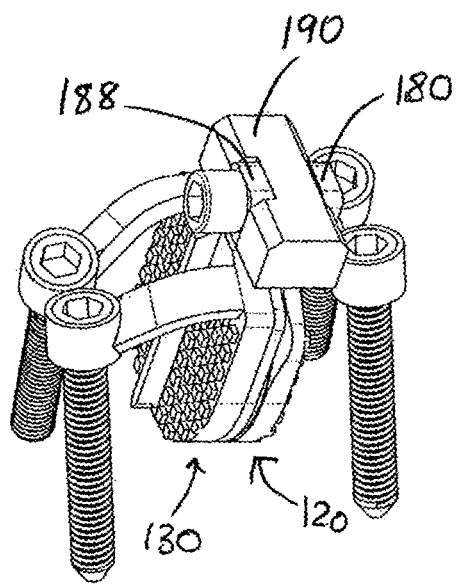

In operation in order to install the implant assembly of FIG. 8 the first and second components 120, 130 are assembled with the male convex bearing surface 122 received in the concave female bearing surface 132 and with the intervertebral plane of each of the intervertebral portions 120a, 130a parallel with one another, the spacer 190 is placed between the first and second projections 180, 188 and the screw 192 is inserted through the hole 189 in the second projection 188, through the hole 193 in the spacer 190 and into the threaded hole 181 in the first projection 180, in order to secure the first and second components together as shown in FIG. 8F. The implant assembly can then be inserted in the intervertebral disc space and the first and second components 120, 130 secured to the respective adjacent vertebrae using bone screws 11. Before fixing the bone screws 11 to the bone, the bendable arms 121, 131 can optionally be adjusted to optimize the position and/or angle of inclination of the bone screws 11. The screw 192 and spacer 190 are detached from the assembly and the first and second components 120, 130 can then articulate relative to one another.

Figure 8G:
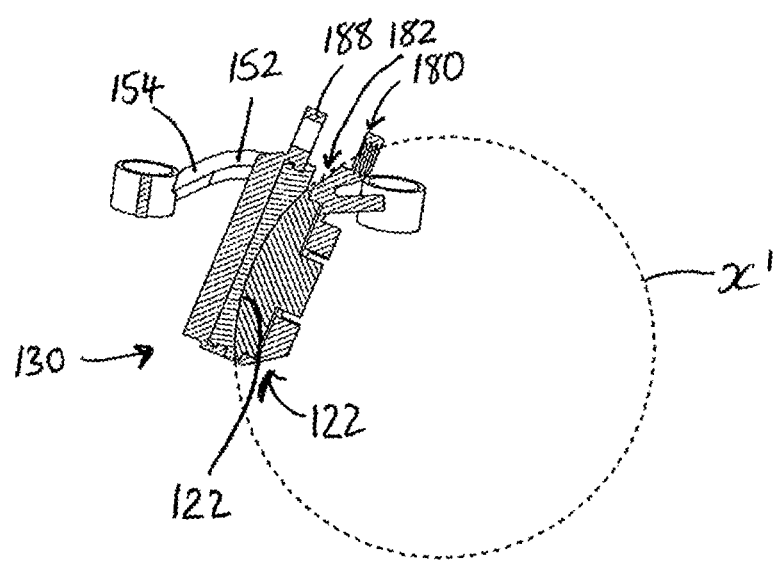
FIG. 8G is a cross-sectional view of the assembly in the sagittal plane.

Referring to FIG. 8G, the articulating surface 122 of the first component 120 has a cross-section in a sagittal plane which forms a convex arc. A notional circle x' is shown in FIG. 8G that aligns with the convex arc of the articulating surface 122 in the sagittal plane. The first side of the proximal portion 182 of the first projection 180 which presents towards the second component 130 when assembled is within the perimeter of the notional circle x' such that the proximal portion 182 of the first projection 180 does not impinge against the second component 130 during flexion of the assembly when implanted. The side of the proximal portion 182 of the first projection 180 which presents towards the second component may alternatively align with the notional circle x', but it should not extend beyond the notional circle x'. Where the convex articulating surface 122 is spherical, as in the present embodiment, the first side of the proximal portion 182 of the first projection 180 is within or aligns with a notional sphere that aligns with the convex articulating surface. The distal portion 183 of the first projection 180 will impinge against the second component 130 at the maximum level of flexion of the prosthetic joint. However, the first component 120 is configured such that during flexion, the first component 120 does not impinge against the second component 130 until at least around 20° of flexion has been achieved from the unflexed state. Like the embodiment of FIGS. 1 to 7, the first component of the embodiment of FIG. 8 is shaped to allow for a natural range of flexion at the joint whilst minimizing the need or preventing the need to remove vertebral bone from the adjacent vertebra before the first component is installed, this shaping being provided by the chamfered profile of the first projection 180 in the sagittal plane.

A plurality of different sized and/or shaped first and second components can be provided as a kit so components that are shaped/sized to suit the vertebral anatomy of the subject can be selected for installation.

It will be understood that changes may be made in the details of the invention without departing from the spirit of the invention, especially as defined in the following claims.

The invention claimed is:

1. A prosthetic intervertebral disc joint assembly for replacing at least a portion of an intervertebral disc between first and second adjacent vertebrae, each vertebra having an anterior side and a posterior side, the assembly having a leading end which leads as the assembly is inserted into the intervertebral space and a trailing end opposite the leading end, and an intervertebral plane passing therebetween which substantially aligns with the intervertebral plane between the adjacent vertebrae when installed, the assembly comprising:

a first component for engaging a first vertebra, the first component having an intervertebral portion insertable between adjacent vertebrae and having a bone-engaging side for engaging an endplate of the first vertebra and an inner side opposite the bone-engaging side, the intervertebral portion of the first component further having a leading end and a trailing end, the inner side of the intervertebral portion of the first component having an articulating surface comprising a generally convex surface;

a second component for engaging a second vertebra, the second component having an intervertebral portion insertable between adjacent vertebrae and having a bone-engaging side for engaging an endplate of the second vertebra and an inner side opposite the bone-engaging side, the intervertebral portion of the second component further having a leading end and a trailing end, the inner side of the intervertebral portion of the second component having an articulating surface comprising a generally concave surface;

wherein the convex articulating surface of the first component is sized and shaped to pivot in the concave articulating surface of the second component, and wherein the first component further comprises a fixation portion for securing the first component to the anterior side of the first vertebra, said fixation portion extending from the trailing end of the intervertebral portion of the first component and wherein the second component further comprises a fixation portion for securing the second component to the anterior side of the second vertebra, said fixation portion extending from the trailing end of the intervertebral portion of the second component, wherein the generally convex articulating surface of the first component is substantially spherically curved and the generally concave articulating surface of the second component is correspondingly substantially spherically curved to match the radius of curvature of the articulating surface of the first component, and wherein the fixation portion of the first component has a proximal portion proximal to the intervertebral portion of the first component, the proximal portion of the first component having an outer side at least part of which presents towards the second component when the assembly is implanted, at least part of the outer side of the proximal portion of the first component being aligned with or substantially within a notional arc, the perimeter of which aligns with the convex articulating surface of the first component in the sagittal plane, such that said at least part of the proximal portion of the first component does not impinge against the second component during flexion of the intervertebral disc joint assembly in use.

2. A prosthetic intervertebral disc joint assembly according to claim 1, wherein the first component has a projection extending from the trailing end of the intervertebral portion of the first component, and wherein the second component has a projection extending from the trailing end of the intervertebral portion of the second component, said projections being adapted to be coupled together during installation of the assembly into an intervertebral space of a subject.

3. A prosthetic intervertebral disc joint assembly according to claim 2, wherein the projection of the first component has a first side which presents towards the second component when the assembly is implanted, at least part of the first side being substantially aligned with or substantially within the notional arc the perimeter of which aligns with the convex articulating surface of the first component in the sagittal plane, such that said at least part of the first side of the projection of the first component does not impinge against the second component during flexion of the intervertebral disc joint assembly in use.

4. A prosthetic intervertebral disc joint assembly according to claim 2, wherein the projection of the first component has a proximal portion proximal to the intervertebral portion of the first component, the proximal portion of the projection of the first component having a first side which presents towards the second component when the assembly is implanted, at least part of the first side of the proximal portion of the projection of the first component being aligned with or substantially within the notional arc, the perimeter of which aligns with the convex articulating surface of the first component in the sagittal plane, such that said at least part of the proximal portion of the projection does not impinge against the second component during flexion of the intervertebral disc joint assembly in use.

5. A prosthetic intervertebral disc joint assembly according to claim 4, wherein the projection of the first component has a distal portion which extends substantially parallel with an intervertebral plane passing through the intervertebral portion of the first component.

6. A prosthetic intervertebral disc joint assembly according to claim 2, wherein the projection of the second component extends substantially parallel with an intervertebral plane passing through the intervertebral portion of the second component.

7. A prosthetic intervertebral disc joint assembly according claim 2, wherein the projections of the first and second components each include a hole for receiving a fixing for coupling the first and second components together.

8. A prosthetic intervertebral disc joint assembly according to claim 2, wherein the assembly further comprises a spacer adapted to be receivable between the projection of the first component and the projection of the second component.

9. A prosthetic intervertebral disc joint assembly according to claim 1, wherein each fixation portion has at least one through hole for receiving a bone screw.

10. A prosthetic intervertebral disc joint assembly according to claim 1, wherein each fixation portion has first and second through holes each through hole having a longitudinal axis, the longitudinal axis of each through hole being angled at a predetermined angle relative to the fixation portion such that first and second bone screws will diverge from one another when installed in the first and second through holes.

11. A prosthetic intervertebral disc joint assembly according to claim 1, wherein the included angle between at least part of the fixation portion of the first component and an intervertebral plane passing through the intervertebral portion of the first component is an obtuse angle.

12. A prosthetic intervertebral disc joint assembly according to claim 1, wherein the included angle between at least part of the fixation portion of the second component and an intervertebral plane passing through the intervertebral portion of the second component is an acute angle.

13. A prosthetic intervertebral disc joint assembly according to claim 1, wherein the radius of curvature of the articulating surface of the first component is predetermined to substantially match that of the subject's natural radius of curvature at the intervertebral disc joint, at least in the sagittal plane.

14. A prosthetic intervertebral disc joint assembly according to claim 1, wherein the radius of curvature of the articulating surface of the first component, at least in the sagittal plane, is predetermined such that once the prosthetic intervertebral disc joint assembly is installed, a common centre of rotation for flexion/extension is provided for the articulating surfaces of the prosthetic intervertebral disc joint assembly and for each of the articulating surfaces of the two facet joints between said first and second vertebrae.

15. A prosthetic intervertebral disc joint assembly according to claim 1, wherein the first component comprises a bearing insert and a supporting body, the bearing insert having the articulating surface thereon and being received, when assembled, in a recess in the supporting body.

\* \* \* \* \*